US006939553B2

(12) United States Patent
Yahiaoui et al.

(10) Patent No.: US 6,939,553 B2
(45) Date of Patent: Sep. 6, 2005

(54) TREATED SUBSTRATE WITH IMPROVED TRANSFER EFFICIENCY OF TOPICAL APPLICATION

(75) Inventors: Ali Yahiaoui, Roswell, GA (US); Robert Cosmo Di Luccio, Titusville, FL (US); Susan Carol Paul, Alpharetta, GA (US); Earl David Brock, Kimberly, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 238 days.

(21) Appl. No.: 09/938,347

(22) Filed: Aug. 24, 2001

(65) Prior Publication Data

US 2002/0058056 A1 May 16, 2002

Related U.S. Application Data

(60) Provisional application No. 60/231,641, filed on Sep. 11, 2000.

(51) Int. Cl.⁷ .................................................. A61F 13/00
(52) U.S. Cl. ...................... 424/402; 424/443; 424/444; 424/446; 424/447; 604/358; 604/307
(58) Field of Search ................................. 424/402, 443, 424/444, 446, 447, 401, 445; 604/307, 358, 304

(56) References Cited

U.S. PATENT DOCUMENTS

| | | | |
|---|---|---|---|
| 3,489,148 A | 1/1970 | Duncan et al. | |
| 3,814,101 A | 6/1974 | Kozak | |
| 4,362,781 A | 12/1982 | Anderson | |
| 4,462,981 A | 7/1984 | Smith | |
| 4,481,243 A | 11/1984 | Allen | |
| 5,254,109 A | 10/1993 | Smith et al. | |
| 5,256,417 A | 10/1993 | Koltisko | |
| 5,607,760 A | 3/1997 | Roe | |
| 5,609,587 A | 3/1997 | Roe | |
| 5,635,191 A | 6/1997 | Roe et al. | |
| 5,643,588 A | 7/1997 | Roe et al. | |
| 5,648,083 A | 7/1997 | Blieszner et al. | |
| 5,871,763 A | 2/1999 | Luu et al. | |
| 5,891,126 A | 4/1999 | Osborn, III et al. | |
| 5,944,705 A | 8/1999 | Ducker et al. | |
| 5,968,025 A | 10/1999 | Roe et al. | |
| 6,107,537 A | 8/2000 | Elder et al. | |
| 6,118,041 A | 9/2000 | Roe et al. | |
| 6,120,488 A | 9/2000 | VanRijswijck et al. | |
| 6,120,783 A | 9/2000 | Roe et al. | |
| 6,153,209 A * | 11/2000 | Vega et al. .................. | 424/400 |
| 6,287,581 B1 * | 9/2001 | Krzysik et al. ............. | 424/402 |

FOREIGN PATENT DOCUMENTS

| | | |
|---|---|---|
| EP | 0040862 | 12/1981 |
| EP | 0 922 457 A1 | 6/1999 |
| WO | 98/20202 | 5/1998 |
| WO | 99/07274 | 2/1999 |
| WO | 99/66793 | 12/1999 |
| WO | 00/10500 | 3/2000 |
| WO | 00/48544 | 8/2000 |
| WO | 01/43717 | 6/2001 |
| WO | 01/49933 | 7/2001 |

OTHER PUBLICATIONS

Patent Cooperation Treaty Search Report from the International Search Authority, International Application No. PCT/US 01/28442 dated Apr. 29, 2002.

* cited by examiner

Primary Examiner—Jyothsna Venkat
(74) Attorney, Agent, or Firm—Nancy M. Klembus

(57) ABSTRACT

The present invention relates to a composite material including a substrate with a first and a second surface, a boundary layer which is comprised of one or more compositions, and a topical application. The boundary layer is applied on the first surface of the substrate, and the topical application is applied to a surface of the boundary layer opposite of the substrate. Transfer efficiency of the topical application is enhanced as the transfer forces necessary to separate the topical application from the boundary layer are lower than the transfer forces necessary to separate the substrate from the boundary layer.

39 Claims, 7 Drawing Sheets

TREATED SUBSTRATE WITH IMPROVED TRANSFER EFFICIENCY OF TOPICAL APPLICATION

This application claims priority from U.S. Provisional Application No. 60/231,641 filed Sep. 11, 2000.

FIELD OF THE INVENTION

This invention relates to a delivery system for the transfer of a topical application to an adjacent surface. A composite includes a boundary layer and a topical application that can be applied to a substrate such as a nonwoven web, such that the topical application may be readily separated from the substrate and subsequently transferred.

BACKGROUND OF THE INVENTION

A number of products made of components including nonwoven fabrics, such as personal care absorbent products, interact with a user's skin. Various skin disorders are often associated with the use of personal care absorbent products. Diaper rash is a prime example of a skin disorder thought to be caused, in part, by friction between a nonwoven fabric and a user's skin. A number of preventative measures have been developed and used over the years, such as the topical application of creams and lotions, in order to cure or prevent diaper rash.

Skin barrier dysfunction is often associated with loss of material and structure in the lipid-containing domains of the skin. One area of skin care product development is lipid replenishment by external applications of lotions supplemented with specific components known to be in-vivo. Use of barrier creams, such as those containing petrolatum or mineral oil, is also common. These barrier creams typically act by occluding the skin with a hydrophobic coating. Petrolatum-based lotions are differentiated from high-value lotions containing botanical extracts in that the latter are intended to deliver an active agent, ostensibly to the skin.

Petrolatum-based lotions effectively prevent or reduce the occurrence of a number of common skin disorders, but typically have required application directly to the skin between each use of a personal care absorbent garment. References which discuss this issue include U.S. Pat. No. 5,635,191 of Roe et al, U.S. Pat. No. 5,606,597 of Roe, and U.S. Pat. No. 5,643,588 of Roe et al. Recently, an application (U.S. Ser. No. 09/559,566, filed Apr. 27, 2000) for personal care absorbent products containing a nonwoven component having petrolatum-based lotions applied thereto has been filed. There remains a need or continues to be a desire for a topical treatment for a nonwoven substrate that can prevent or reduce the occurrence of a number of common skin disorders associated with disposable personal care absorbent garments. There is also the need or desire to maximize application transfer to the skin at minimum topical application add-on with demonstrable skin health benefits. There is also a need or desire for an efficient and enhanced method of transferring topical applications, including petrolatum-based lotion, from a nonwoven substrate to a user's skin.

SUMMARY OF THE INVENTION

In response to the discussed difficulties and problems encountered in the prior art, a new method and composite for enhancing the transfer efficiency of a topical application from a nonwoven substrate to an adjacent or secondary surface, such as a user's skin, has been discovered. While maintaining acceptable fluid handling performance and skin hydration for the nonwoven substrate, the surface treatment composition is capable of enhancing transfer efficiency of the topical application to the user's skin upon skin/substrate contact.

The present invention relates to a combination for surface treatment of a substrate used in personal care product applications. The surface treatment not only provides a topical delivery system effective in transferring the topical application to a secondary surface, but also significantly enhances the efficiency thereof, thereby providing for a lower minimum topical application add-on to achieve demonstrable benefits at or on a secondary surface.

The present invention is directed to a composite material that includes a substrate, a boundary layer, and a topical application, wherein a first surface of the boundary layer is applied on a first surface of the substrate, and wherein the topical application is applied to the second surface of the boundary layer. For improved transfer efficiency of the topical application to a secondary surface, the boundary layer and the topical application have a low affinity towards the other such that the transfer forces necessary to separate the topical application from the boundary layer are lower than the transfer forces necessary to separate the boundary layer from the substrate. Transfer efficiency is also improved when a boundary layer is present between the topical application and the substrate as compared to when the topical application is placed directly onto the substrate, i.e. the boundary layer is not present. It is also contemplated that the boundary layer may have a lower melt temperature than the substrate, whereby the boundary layer liquifies or begins to liquify when exposed to a temperature of at least about 25° C. Liquification of the boundary layer generally weakens the boundary layer and lowers the transfer forces which are necessary to allow the topical application to separate from the substrate and to be transferred.

To enhance transfer efficiency of the topical application, the boundary layer may include more than one layer of compounds having low affinity towards each other, thereby allowing the topical application and a portion of the boundary layer to separate from a second portion of the boundary layer rather than necessitating separation at the topical application/boundary layer interface. The ability to create boundary layer/boundary layer separation will allow the use of compounds in the boundary layer which, in light of the enhanced transfer efficiency goals of the invention, may otherwise be unsuitable for use (e.g. due to high affinity) with a topical application.

To further enhance transfer efficiency, the boundary layer may be applied to the substrate and the topical application may be applied to the second surface of the boundary layer in a variety of patterns. To achieve maximum transfer efficiency it is not necessary for all of the first surface of the substrate to be covered by the boundary layer or all of the second surface of the boundary layer to be covered by the topical application.

It is contemplated that the invention will enhance the transfer efficiency of lotions or ointments from a nonwoven to a user's skin as well as enhancing the transfer efficiency in a variety of other applications, including but not limited to industrial applications, such as the delivery of polishes, cleaning or cleansing agents and the like from a nonwoven or other substrate.

The invention is also directed to a method of enhancing the transfer efficiency of a topical application from a substrate to a secondary surface. The method includes the provision of a substrate, the application of a boundary layer treatment to the substrate, the application of a topical application to the boundary layer, and subjecting the boundary layer to at least one condition which facilitates separation of the topical application from the substrate and promotes transfer of the topical application to a secondary surface which is adjacent to the boundary layer and topical application.

With the foregoing in mind, it is a feature and advantage of the invention to provide a composite material having a surface treatment which enhances transfer efficiency of a topical application to a secondary surface, preferably skin, upon secondary surface/substrate contact.

It is also a feature and advantage of the invention to provide an enhanced method of transferring a topical application from a substrate to skin.

DEFINITIONS

Figure 1:
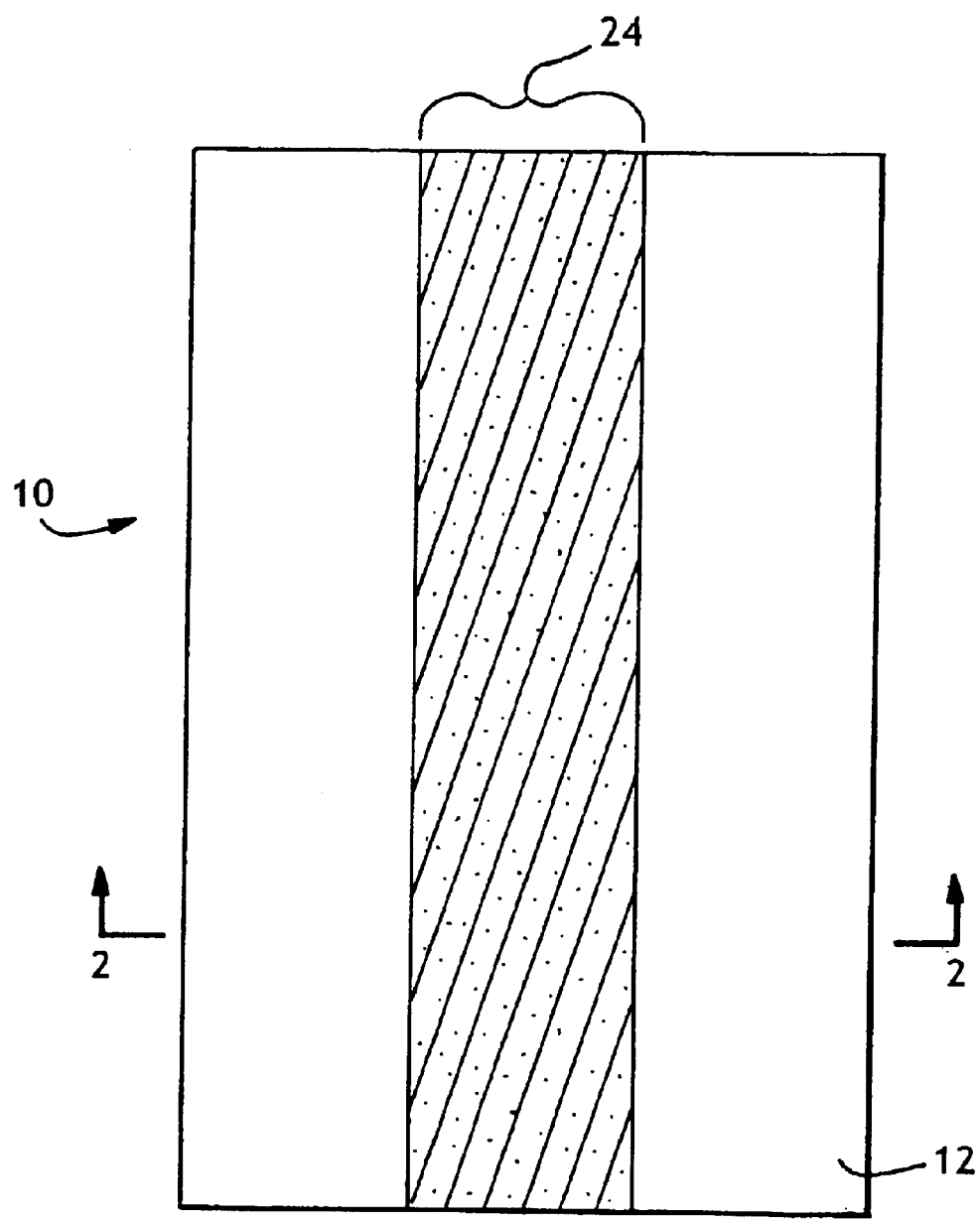
FIG. 1 is a top plan view of one embodiment of a composite material in accordance with the present invention.

As used herein the following terms have the specified meanings, unless the context demands a different meaning, or a different meaning is expressed; also, the singular generally includes the plural, and the plural generally includes the singular unless otherwise indicated.

As used herein, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof.

As used herein, the term "fabric" refers to all of the woven, knitted and nonwoven fibrous webs.

As used herein, the term "layer" when used in the singular can have the dual meaning of a single element or a plurality of elements.

As used herein, the terms "lotion" or "ointment" are generally interchangeable and mean a formulation, powder or combination thereof comprising skin health ingredients, or compositions which are skin compatible but which do not in and of themselves provide skin health or skin wellness benefits.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface.

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein "multi-layer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy. Multi-layer laminates may also have various numbers of meltblown layers or multiple spunbond layers in many different configurations and may include other materials like films (F) or coform materials, e.g. SMMS, SM, SFS, etc.

As used herein the terms "nonwoven" and "nonwoven fabric or web" mean a web having a structure of individual fibers, filaments or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "personal care product" or "personal care absorbent product" means diapers, training pants, swim wear, absorbent underpants, baby wipes, adult incontinence products, sanitary wipes, wet wipes, feminine hygiene products, wound dressings and bandages.

As used herein, the term "petrolatum" refers to a semi-solid mixture of hydrocarbons obtained from petroleum, such as, but not limited to Glenpure L White Petrolatum, USP available from Glenn Corporation, a business having offices in St. Paul, Minn.

As used herein, the term "skin" refers to the outermost exposed layer of a mammal's dermis or epidermis, and may be a wound.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

As used herein, the term "topical application" means any overlayer type of material surface modification, including, but not limited to any polishes, cleaning or cleansing agents, and the like, as well as any lotions, ointments, powders or combinations thereof. For purposes of this application, the term "surface enhancing agent" is generally interchangeable with the term topical application.

As used herein, the term "transfer forces" means any of the forces which can cause separation of two or more layers of the composite material of the present invention. As used herein the term "transfer forces" may specifically refer to, but is not limited to, shear forces, peel forces, preferential chemical affinity to one substance or surface over another substance or surface, or other force or combination of forces which generally enable the separation of the topical application from all or part of the boundary layer or the separation of one layer of the boundary layer from a second layer of the boundary layer.

These terms may be defined with additional language in the remaining portions of the specification.

DETAILED DESCRIPTION OF THE INVENTION

Although the description of the invention is focused on the transfer of a topical application to the skin of a user, it is contemplated that one skilled in the art will recognize that the delivery system described herein may be used with any topically treated substrate for which a suitable boundary layer composition is available and for which it is desired to improve the transfer efficiency of the topical treatment or application to a secondary surface.

While the topical administration of skin treatment compositions or applications to the skin of mammals, especially humans, is known to protect the skin by preserving and restoring the natural integrity of the skin, efficient transfer of topical applications from absorbent articles by way of weak boundary layer transfer is not known to have been previously achieved. Efficient transfer of topical applications not only ensures that the desired surface receives an effective amount of the application, but also minimizes the amount of application add-on which is necessary. The minimization of add-on contributes to a lower production cost. Compositions and methods are provided by the present invention for the enhanced transfer efficiency of topical applications.

Figure 2:
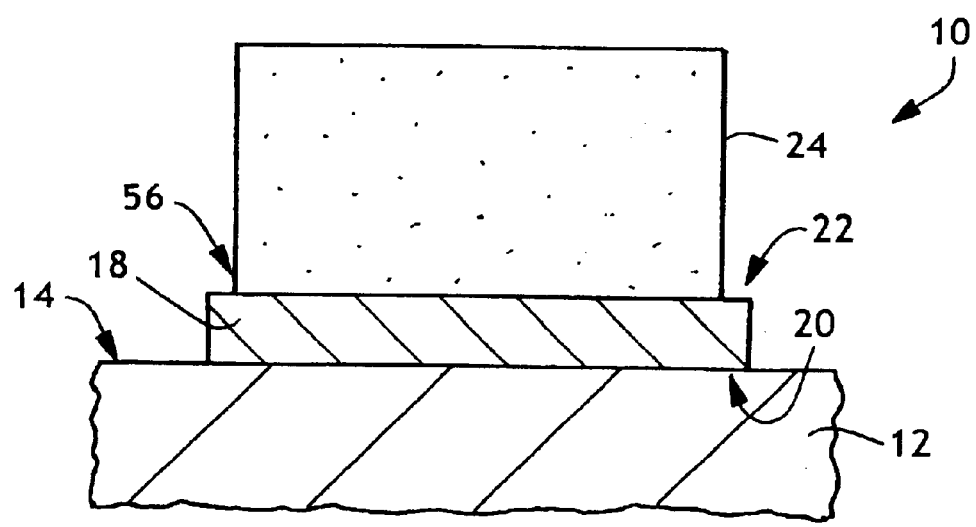
FIG. 2 is a cross-section view of the composite material shown in FIG. 1 taken along line 2—2.

FIGS. 1 and 2 illustrate the simplest form of the composite material which is the present invention. As shown, the composite material 10 comprises a substrate 12, said substrate having a first surface 14, and a second surface 16 (shown in FIG. 4) opposite the first surface 14. The composite material further comprises a boundary layer 18, said boundary layer being comprised of one or more compounds, and having a first surface 20 and a second surface 22 opposite the first surface 20 of the boundary layer. The first surface 20 of the boundary layer 18 is applied to the first surface 14 of the substrate 12. The composite material also comprises a topical application. As illustrated, the topical application 24 is applied to the surface 22 of the boundary layer 18 opposite of the substrate. The topical application 24 is shown in FIG. 1 by diagonal lines, however, this is done only to distinguish the region to which topical application 24 is applied to the substrate 12 and not to suggest or limit the manner in which the topical application may be applied, as discussed below. The composite material is created in such a manner that the transfer forces necessary to separate the topical application 24 from the boundary layer 18 are lower than the transfer forces necessary to separate the substrate 12 from the boundary layer 18 (or the topical application from the substrate if the topical application were applied directly thereto), whereby transfer efficiency of the topical application is enhanced.

Figure 3:
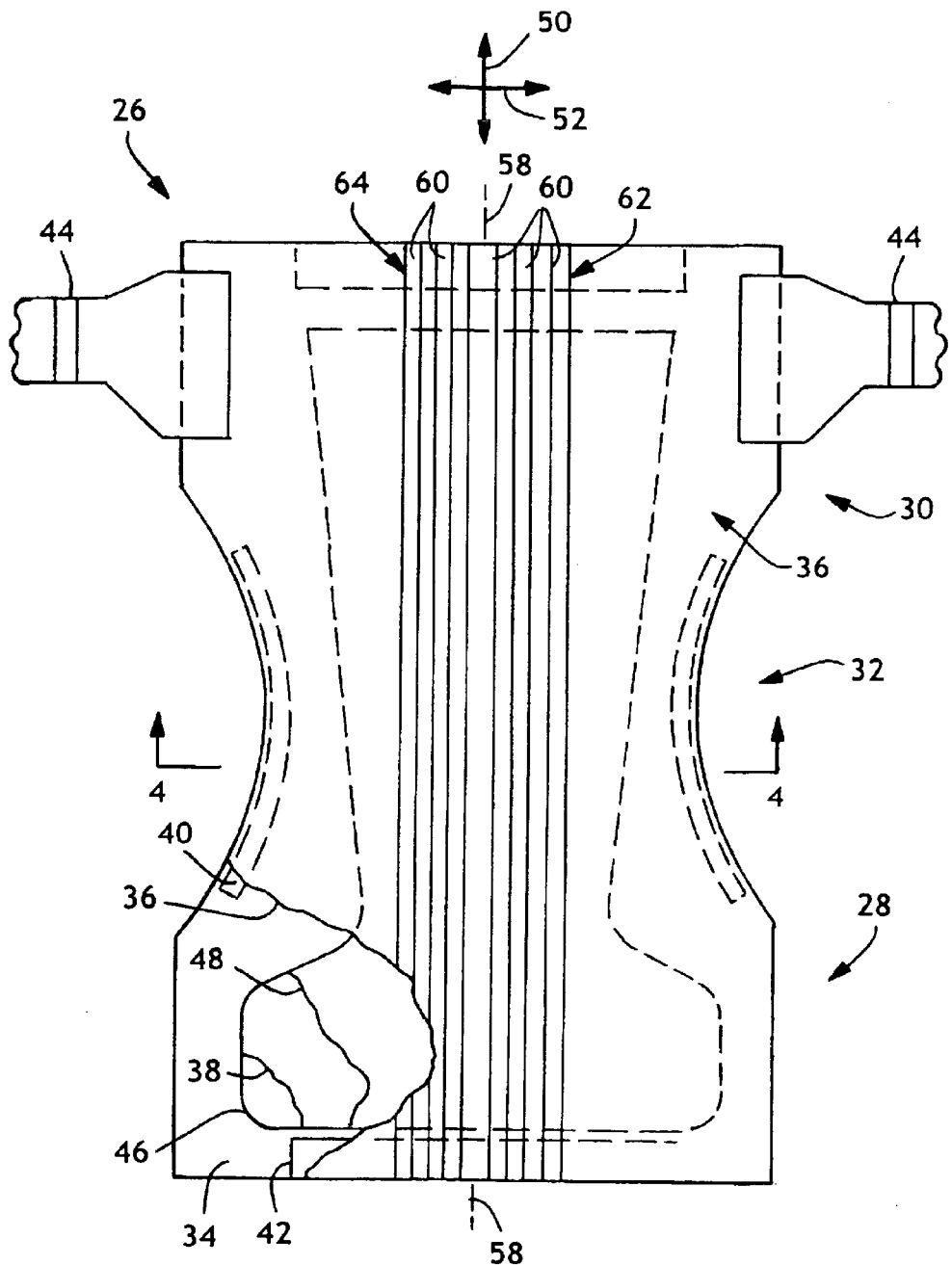
FIG. 3 representatively shows a partially cutaway, top plan view of an absorbent article according to one embodiment of the invention.
Figure 4:
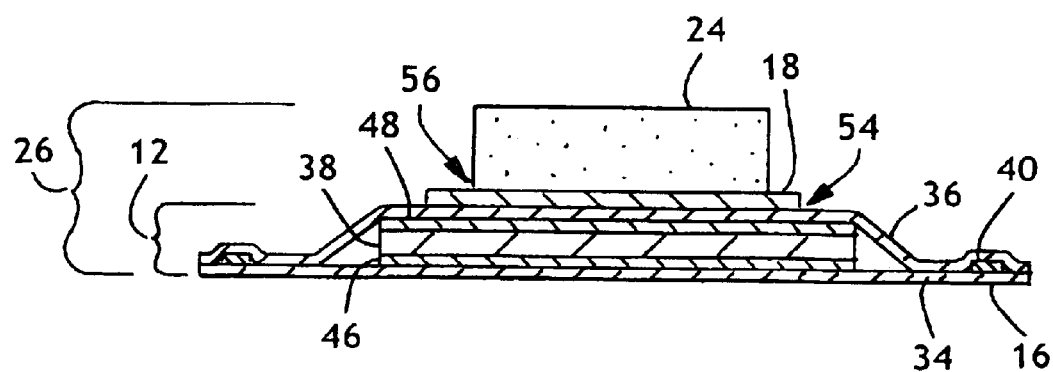
FIG. 4 representatively shows a sectional view of the absorbent article of FIG. 3 taken along line 4—4.

While illustrated as a single layer in FIGS. 1 and 2, the substrate of the composite material may be a multi-layer laminate, as shown in FIGS. 3 and 4. An example of a multi-layer laminate is an embodiment wherein some of the layers are spunbond and some meltblown such as a spunbond/meltblown/spunbond (SMS) laminate as disclosed in U.S. Pat. No. 4,041,203 of Brock et al., U.S. Pat. No. 5,169,706 of Collier et al., and U.S. Pat. No. 4,374,888 of Bornslaeger. Such substrates usually have a basis weight of from about 0.1 to 12 osy (6 to 400 gsm), or more particularly from about 0.75 to about 3 osy.

The remainder of the detailed description will be made in the context of a disposable diaper article which is adapted to be worn by infants about the lower torso. It is readily apparent, however, that the composite material of the present invention would also be suitable for use as or in other types of absorbent articles, such as feminine care pads, incontinence garments, training pants, and the like. As above, it is also apparent that the composite material of the present invention is suitable for use as a wipe, such as one that is used to more efficiently transfer a topical application or surface enhancing agent such as a polish, cleaning or cleansing agent or the like to a secondary surface. In addition, the invention will be described in the context of its various configurations. It should be appreciated that alternative arrangements of the invention can comprise any combination of such configurations, including those absorbent articles or personal care products whose substrate is comprised of a single layer. As such, the use of a desired embodiment, a diaper, for ease in understanding and describing the invention shall not, in any manner, limit the scope of the invention.

It is important to understand, that unless otherwise indicated, reference to a substrate in the context of an absorbent article or personal care product, and more particularly a diaper, may, depending on the circumstances, refer to the entire structure of the article or product if the article is a single layer (as best seen in FIGS. 1 and 2), the layer of the article or product which contacts the wearer if the article is comprised of more than one layer (as best seen in FIGS. 3 and 4) or, generally, the surface of the article or product which contacts the wearer.

FIG. 3 is a representative top plan view of an integral absorbent garment article or personal care product, such as disposable diaper 26, according to one embodiment of the present invention in its flat-out, uncontracted state (i.e., with all elastic induced gathering and contraction removed). Portions of the structure are partially cut away to more clearly show the interior construction of the absorbent article or diaper 26, and the surface of the diaper which contacts the wearer is facing the viewer. FIG. 4 representatively shows a sectional view of the absorbent article of FIG. 3 taken along line 4—4. With reference to FIGS. 3 and 4, the disposable diaper 26 generally defines a front waist section 28, a rear waist section 30, and an intermediate section 32 which interconnects the front and rear waist sections. The front and rear waist sections 28 and 30 include the general portions of the article which are constructed to extend substantially over the wearer's front and rear abdominal regions, respectively, during use. The intermediate section 32 of the article includes the general portion of the article which is constructed to extend through the wearer's crotch region between the legs.

A desired embodiment of the composite material incorporated in an absorbent article includes a substrate having a vapor permeable backsheet or outercover 34, a liquid permeable liner or topsheet 36 positioned in facing relation with the backsheet 34, and an absorbent body 38, such as an absorbent pad, which is located between the backsheet 34 and the topsheet 36. The backsheet 34 defines a length and a width which, in the illustrated embodiment, coincide with the length and width of the diaper 26. The absorbent body 38 generally defines a length and width which are less than the length and width of the backsheet 34, respectively. Thus, marginal portions of the diaper 26, such as marginal sections of the backsheet 34, may extend past the terminal edges of the absorbent body 38. In the illustrated embodiments, for example, the backsheet 34 extends outwardly beyond the terminal marginal edges of the absorbent body 38 to form side margins and end margins of the diaper 26. The topsheet 36 is generally coextensive with the backsheet 34 but may optionally cover an area which is larger or smaller than the area of the backsheet 34, as desired. The backsheet 34 and topsheet 36 are intended to face the garment and body of the wearer, respectively, while in use.

The permeability of the backsheet is configured to enhance the breathability of the absorbent article to reduce the hydration of the wearer's skin during use without allowing excessive condensation of vapor, such as urine, on the garment facing surface of the backsheet 34 which can undesirably dampen the wearer's clothes.

To provide improved fit and to help reduce leakage of body exudates from the diaper 26, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIGS. 3 and 4, the diaper 26 may include leg elastics 40 which are constructed to operably gather and shirr the side margins of the diaper 26 to provide elasticized leg bands which can closely fit around the legs of the wearer to reduce leakage and provide improved comfort and appearance. Similarly, waist elastics 42 can be employed to elasticize the end margins of the diaper 26 to provide elasticized waists. The waist elastics are configured to operably gather and shirr the waist sections to provide a resilient, comfortably close fit around the waist of the wearer. In the illustrated embodiments, the elastic members are illustrated in their uncontracted, stretched condition for the purpose of clarity.

Fastening means, such as hook and loop fasteners 44, are employed to secure the diaper on a wearer. Alternatively, other fastening means, such as buttons, pins, snaps, adhesive tape fasteners, cohesives, mushroom-and-loop fasteners, or the like, may be employed.

The diaper 26 may further include other layers between the absorbent body 38 and the topsheet 36 or backsheet 34. For example, as representatively illustrated in FIGS. 3 and 4, the diaper 26 may include a ventilation layer 46 located between the absorbent body 38 and the backsheet 34 to insulate the backsheet 34 from the absorbent body 38 to improve air circulation and effectively reduce the dampness of the garment facing surface of the backsheet 34. The ventilation layer 46 may also assist in distributing fluid exudates to portions of the absorbent body 38 which do not directly receive the insult. The diaper 26 may also include a surge management layer 48 located between the topsheet 36 and the absorbent body 38 to prevent pooling of the fluid exudates and further improve air exchange and distribution of the fluid exudates within the diaper 26.

In the most desired embodiment, no surfactant will be added to or incorporated into the composite material of the present invention, however, in an alternative embodiment, the substrate or topsheet 36 of the diaper 26 may also be treated with a surfactant to promote wettability of the substrate, thereby promoting the wicking of moisture away from the surface of the user's skin and improved skin health conditions.

In the alternative embodiment incorporating a surfactant, the fabric of the topsheet 36 is surface treated with a surfactant such as that commercially available from Union Carbide Chemicals and Plastics Company, Inc., of Danbury, Conn., U.S.A. under the trade designation TRITON X-102. Alternatively, the fabric may be surface treated with about 0.3 weight percent of a surfactant mixture which contains a mixture of AHCOVEL Base N-62 and GLUCOPON 220UP surfactant in a 3:1 ratio based on a total weight of the surfactant mixture. Other possible classes of surfactants include MASIL SF 19 and DC 193 Surfactant. The AHCOVEL Base N-62 is purchased from Uniqema (A division of ICI, and having offices in New Castle, Del.), and includes a blend of hydrogenated ethoxylated castor oil and sorbitan monooleate. The GLUCOPON 220UP is purchased from Cognis Corporation and includes an alkyl polyglycoside. MASIL SF 19 and DC 193 Surfactant are purchased from BASF (Gumee, Ill.), and Dow Corning (Midland, Mich.), respectively. MASIL SF 19 and DC 193 Surfactant are examples of typical ethoxylated polyalkylsiloxanes. The surfactant may be applied by any conventional means, such as saturation, spraying, printing, roll transfer, slot coating, brush coating, internal melt addition or the like. The surfactant may be applied to the entire topsheet 36 or may be selectively applied to particular sections of the topsheet 36, such as the medial section along the longitudinal centerline of the diaper, to provide greater wettability of such sections.

The diaper 26 may be of various suitable shapes. For example, the diaper may have an overall rectangular shape, T-shape or an approximately hour-glass shape. In the shown embodiment, the diaper 26 has a generally I-shape. The diaper 26 further defines a longitudinal direction 50 and a lateral direction 52. Other suitable diaper components which may be included in absorbent articles incorporating the present invention include containment flaps, waist flaps, elastomeric side panels, and the like which are generally known to those skilled in the art.

Examples of diaper configurations suitable for use in connection with the instant application which may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference in their entireties.

The various components of the diaper 26 are integrally assembled together employing various types of suitable attachment means, such as adhesive, sonic bonds, thermal bonds or combinations thereof. For example, the topsheet 36 and backsheet 34 may be assembled to each other and to the absorbent body 38 with lines, not shown, of adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 40 and 42, fastening members 44, and ventilation and surge layers 46 and 48 may be assembled into the diaper article by employing the above-identified attachment mechanisms.

Figure 5:
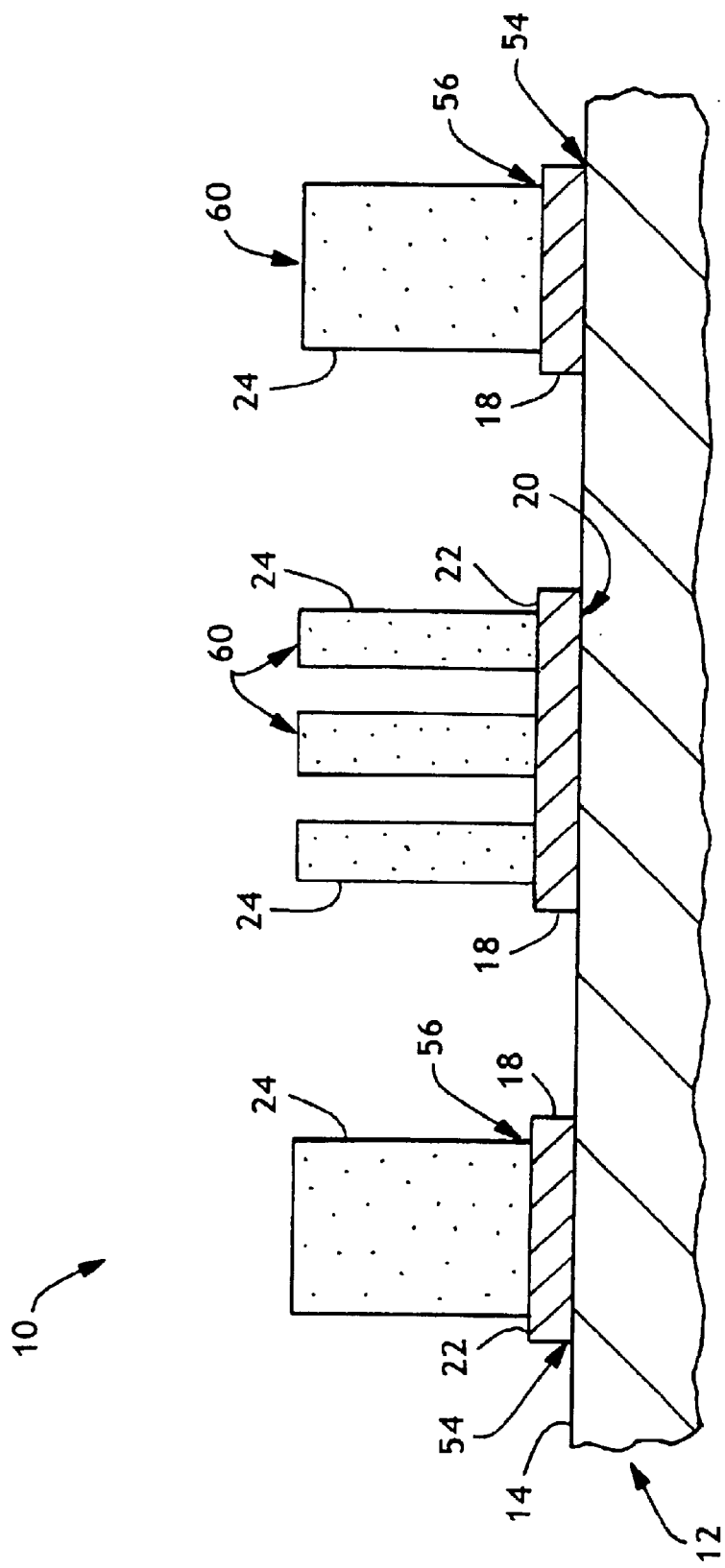
FIG. 5 representatively shows a cross-sectional view of a composite material according to another embodiment of the invention.
Figure 6:
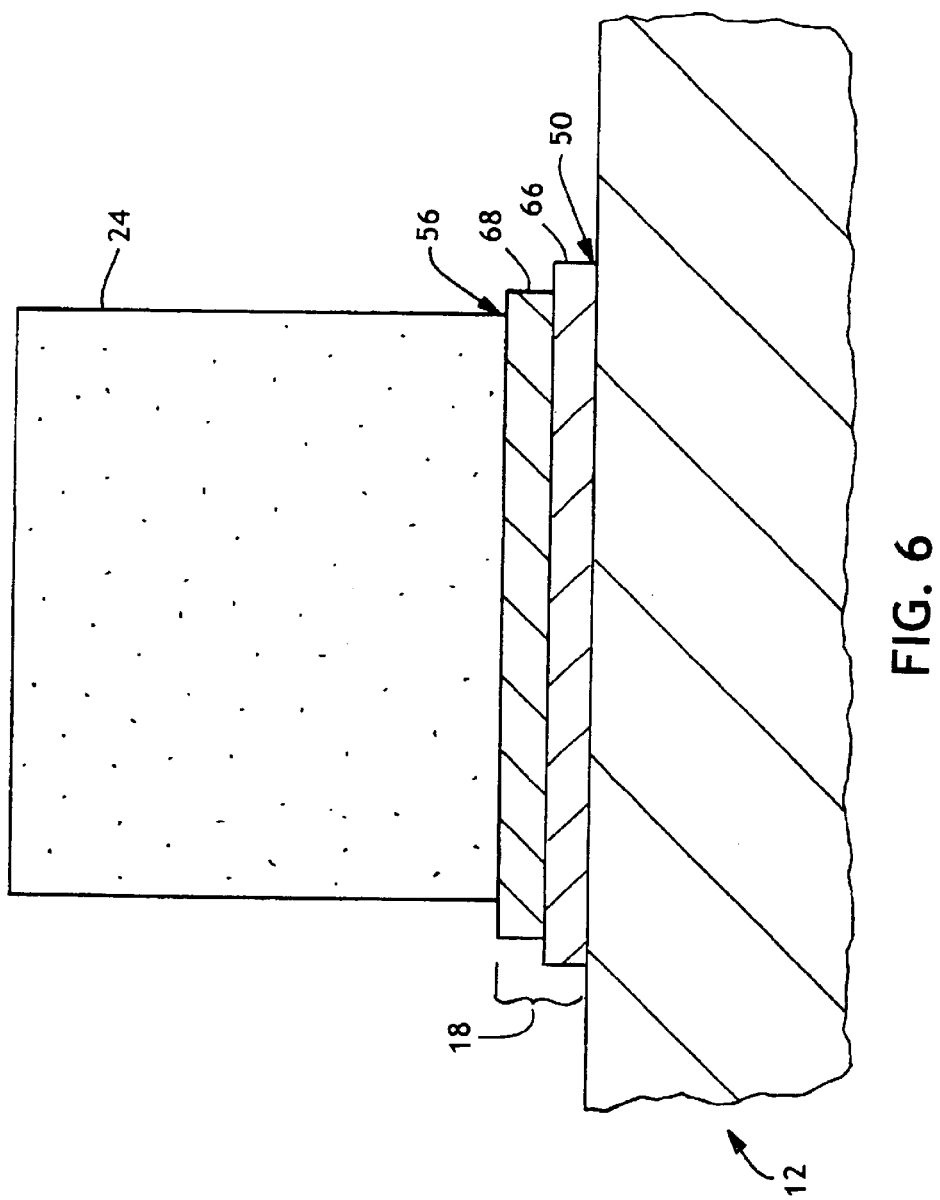
FIG. 6 representatively shows a sectional view of a composite material according to another embodiment of the present invention, wherein the boundary layer is shown as comprised of two layers.

FIGS. 2 and 4 through 6 illustrate that the composite material further includes a boundary layer 18, having a first surface 20 and a second surface 22, and a topical application 24. While the substrate may be more or less complex than that described with respect to and illustrated in FIGS. 3 and 4, the substrate representing the absorbent article or diaper 26 in FIGS. 5 and 6 is shown as monolayer substrate for simplicity purposes only.

As shown in FIGS. 4 through 6, the first surface 20 of boundary layer 18 is applied to the surface 36 of the diaper which contacts the wearer (body-facing surface). The area where the boundary layer 18 and the body-facing surface 36 of the diaper come into contact with each other is defined as the boundary layer/substrate interface 54. As further illustrated, the topical application 24 is applied to the second surface 22 of the boundary layer 18 thereby creating a boundary layer/topical application interface 56.

As above, the boundary layer 18 is applied to the body-facing surface or topsheet 36 of the diaper. Any of a variety of application methods that evenly distribute the boundary layer compounds having a molten or liquid consistency can be used. Suitable methods include, but are not limited to, spraying, slot coating, printing (such as flexographic printing), coating (such as gravure coating), extrusion, or combinations of these methods, such as spraying the composition on a rotating surface, then transferring the composition to the body-facing surface 36 of the diaper 26. It is also possible to prepare a substrate which has an uneven or non-uniform distribution of boundary layer on its surface. Furthermore, it is also possible to use an internal melt additive such as an polyalkylsiloxane or an alkylated fatty ester. The internal melt additive is meant to exude to the surface of the nonwoven fiber, thereby providing a boundary layer on which a topical lotion or ointment can subsequently be applied on. Typical examples of polyalkysiloxanes are DC 200 Silicone fluids (Dow Corning, Midland, Mich.), which are also available from Dow Corning, as compounded concentrates in polyolefins known as Masterbach MB50-001 Silicone and Masterbach MB50-002 Silicone. Typical examples of alkylated fatty esters are sorbitan mono, di or tri-oleates and their stearates analogs, which are available from Uniqema.

The boundary layer 18 may be applied to the entire body-facing surface 36 of the diaper 26 or may be selectively applied to portions thereof. If applied to only a portion of the body-facing surface 36 of the diaper, the boundary layer 18 may be applied in a patterned orientation or in one or more strips 60. Although the figures illustrate the boundary layer as a continuous or substantially continuous application in the machine direction of the diaper, it is understood and contemplated that the boundary layer may be applied in any continuous or discontinuous pattern, including but not limited to, continuous or discontinuous lines in the machine direction, cross-direction, or diagonal orientations, sinusoidal waves or discrete dots, and the like, provided that the pattern is such that a topical application may be applied thereto.

It is desirable that the boundary layer be applied to the body-facing surface 36 of the diaper 26 in a strip or pattern aligned with or centered on the longitudinal centerline 58 of the absorbent article 10, so that the strip or pattern runs through the intermediate section 32 (i.e. crotch region) of the diaper 26. It is more desirable for the boundary layer to be applied to the body-facing surface 36 of the diaper 26 in a plurality of strips 60. Depending on the total surface area, it is often desirable that the number of strips which comprise the boundary layer 18 generally be between 1 and 60, more desirably between 4 and 12, and even more desirably between 4 and 8. The dimensions of the strips or patterns will vary with the different absorbent articles or personal care products to which the boundary layer 18 is applied, however, it is desirable that the boundary layer 18 be approximately four inches in width as measured from the outside edge of the two outermost strips or patterns of boundary layer from the centerline 58 (e.g. from the outside of strip 62 to outside of strip 64 as best seen in FIG. 3—assuming that the width of the boundary layer is equal to the width of the topical application shown in the illustration). It is not necessary that the strips of the boundary layer 18 be uniform in width, however, it is desirable that the strips of the boundary layer 18 each be about 0.1 mm to about 100 mm in width, more desirably about 0.5 mm to about 40 mm in width, and even more desirably about 1 mm to about 7 mm in width. It is also desirable that each of the strips of the boundary layer have about 0.1 mm to about 100 mm of separation between each other, more desirably about 0.5 mm to about 40 mm of separation, and even more desirably about 1 mm to about 7 mm of separation between each other. The separation of the boundary layer strips or patterns need not be uniform, but should be of sufficient width to allow the layers of the substrate to be adhered to each other, as necessary. As with the width and the separation, the strips or patterns of boundary layer may be applied in a variety of heights. It is desirable that each of the strips or patterns of the boundary layer be about 0.1 mm to about 0.5 mm in height, more desirably about 0.1 mm to about 0.3 mm in height, and even more desirably be about 0.1 mm to about 0.2 mm in height.

With the exception of those embodiments of the invention which incorporate a multi-layer boundary layer (such as the embodiment shown in FIG. 6), the boundary layer 18 of the present invention can be applied to the body-facing surface of a substrate at any point during assembly of an absorbent article. For example, the raw material web being formed into the substrate may be treated with the boundary layer composition before the web is processed into the substrate; the body-facing surface of the substrate may be treated with the boundary layer composition before being incorporated into the absorbent article; and, the body-facing surface of the substrate may be treated with the composition after the substrate has been incorporated into the absorbent article. Those embodiments of the invention which incorporate a multi-layer boundary layer may have the first layer 66 of the boundary layer 18 applied to the body-facing surface 36 of the substrate at any point during the assembly of the absorbent article or personal care product; however, the second layer 68 of the boundary layer 18 may only be applied post-extrusion of the substrate and inherently after the first layer 66. The second layer 68 of boundary layer 18 may be applied to the first layer 66 by any of a variety of application methods that evenly distribute the boundary layer compounds having a molten or liquid consistency. Suitable methods for applying the second layer 68 include, but are not limited to, all of those listed above except for extrusion.

Examples of boundary layer compounds which are suitable for use in the present invention include, but are not limited to, triglyceride derivatives and co-formulations, sorbitan ester derivatives and co-formulations, dimethicones, hydrocarbon emollients such as myristyl myristate (Cetiol 1414 E, made by Cognis Corporation), long chain alcohols and acids having carbon chain lengths up to 104 carbons, ethoxylated alcohols or acids having carbon chain lengths up to 104 carbons, highly branched polyethylene oligomers, oxidized hydrocarbons (such as polyethylene and polypropylene), linear polyethylene oligomers, polyvinyl acetate and polyvinyl acetate silicone derivatives.

After the boundary layer 18 is applied to the body-facing surface 36 of the diaper 26, a topical application 24 is applied to the boundary layer 18. Although some topical applications may be more or less desirable than others based on their affinity or lack of thereof to certain compounds (i.e. those which may comprise the boundary layer), nothing in this disclosure is intended to limit the scope of topical applications which may be used in the present invention.

Topical application 24 may be applied to the entire second surface 22 of the boundary layer 18 or may be selectively applied (i.e. in strips or patterns) to particular sections of the second surface 22 of the boundary layer 18, to provide greater lubricity of such sections and to transfer such lotion to the wearer's skin. Alternatively, as representatively illustrated in FIG. 5, the second surface 22 of the boundary layer 18 may include multiple strips of the topical application 24 applied thereto. It is to be understood that the topical application may be applied to the boundary layer 18 in a variety of manners. For example, one strip or pattern 60 of topical application 24 may be applied to each strip or pattern of boundary layer 18 or multiple strips and/or patterns 60 of the topical application 24 may be applied to each strip or pattern of boundary layer 18 depending on the size of each. The patterns or strips 60 of topical application 24 may extend the full length of the strips of boundary layer 18 or only a portion thereof. The length of the strips 60 of topical application 24 will depend, in part, upon the length of the boundary layer. It is desirable for the topical application 24 to extend substantially the entire length of the boundary layer 18 to which it is applied. As above, in a desired embodiment, the boundary layer 18 will extend substantially the entire length of the personal care product 10, and, consequently, it is desirable that the topical application 40 extend substantially the entire length of the personal care product 10 as well.

The strips or patterns 60 of topical application 24 may also define a width of from about 0.2 to about 1 centimeters. It is desirable that the strips 60 have a width of from about 0.2 to about 0.5 centimeters, more desirable from about 0.2 to about 0.4 centimeters, and even more desirable from about 0.2 to about 0.3 centimeters. It is also desirable that the strips 60 of topical application 24 be separated by a distance of about 0.2 to 0.5 centimeters, and more desirably by a distance of about 0.2 to about 0.4 centimeters. It is also desirable that the strips 60 of topical application 24 have a height of about 0.1 mm to 0.3 mm, and more desirably a height of about 0.2 mm to about 0.3 mm. It is possible to prepare an absorbent article or personal care product which has an uneven or non-uniform distribution of topical application 24 on its boundary layer 18.

The topical application may be applied to the second surface 22 of the boundary layer 18 in any of many well known manners. A preferred method to uniformly apply the topical application to the body-facing surface of the boundary layer 18 is spraying or slot coating, because it is, for most practical purposes, the most exact process and offers maximum control of the topical application distribution and transfer rate. However, other suitable methods, also include printing (such as flexographic printing), coating (such as gravure coating), extrusion, or combinations of these methods, such as spraying the composition on a rotating surface, then transferring the composition to the second surface 22 of the boundary layer 18.

For example, the topical application may be applied to the boundary layer by (a) heating the topical application to a temperature above the melting point of the topical application, causing the application to melt, (b) uniformly applying the melted topical application to the body-facing surface of the boundary layer; and (c) resolidifying the deposits of the melted topical application. Desirably, resolidification of the deposits occurs almost instantaneously, without the need for external cooling means such as chill rolls. This can occur if the topical application is heated to a temperature only slightly above or at the melting point of the topical application. However, external means such as chill rolls, either before or after the application of melt, can be used if desired to accelerate resolidification. As used herein, the terms "liquify" and "melt" are generally interchangeable and are intended to include the stage of liquification and/or melting at which the substance or formulation undergoing the transformation is but partially transformed.

Whether applied in a strip or a pattern, the topical application 24 should cover a sufficient amount of the surface area of the boundary layer 18 and in turn the substrate to ensure adequate topical application transfer to the skin and reduced abrasion between the diaper or substrate and the wearer's skin. Desirably, the topical application is applied to at least about 10 percent and more desirably at least about 30 percent of the boundary layer 18, and in turn to at least about 5 percent and more desirably at least about 25 percent of the body-facing surface of the substrate for enhanced transfer.

The topical application can be applied to the boundary layer at any add-on level which provides the desired transfer benefit. For example, the total add-on level of the topical application can be from about 0.05 to about 100 $mg/cm^2$, desirably from about 1 to about 50 $mg/cm^2$ and more desirably from about 10 to about 40 $mg/cm^2$ for improved performance. The add-on amount will depend upon the desired effect of the topical application on the attributes of the personal care product and upon the specific topical application. It is desired to minimize the amount of topical application which is in contact with the boundary layer at interface 56, yet increase the surface area of topical application contained in the article or product, thereby enabling greater transfer efficiency. In one embodiment of the present invention, the width of the topical application strips is reduced while maintaining the same amount of topical application add-on, thereby increasing the height of the strips 60 and in turn increasing surface area.

Examples of topical applications which are suitable for use in the present invention include natural and synthetic fats, oils and waxes, polyolefin oligomers, fatty acids, fatty alcohols, surfactants, perfumes, emulsions, emollients, humectants, and any cosmetically accepted topical ingredients as well as OTC products listed in 21 C.F.R. Parts 344, 346, 347, 348 and 352, including, but not limited to, urea hydrogen peroxide, vasoconstrictors actives (such as 0.10–1.25% ephedrine sulfate, 0.005–0.01% epinephrine, 0.05–0.01% epinephrine hypochloride, and 0.25% phenylephrine hypochloride), keratolytic actives (such as alcloxa and resorcinol), analgesic, anesthetic, and antipruritic actives (such as benzocaine, lidocaine, 0.10–0.30% camphor, 1.0–5.0% juniper tar, and 0.10–1.0% menthol), astringent actives (such as calamine, witch hazel, and zinc oxide), local anesthetic actives (such as benzocaine, benzyl alcohol dibucaine, dibucaine hydrochloride, dyclonine hydrochloride, lidocaine, pramoxine hydrochloride, tetracaine, tetracaine hydrochloride), analgesic, anesthetic, and skin protectants (such as aluminum hydroxide, calamine, cocoa butter, cod liver oil, glycerin, hard fat, kaolin, lanolin, mineral oil, petrolatum, shark liver oil, topical starch, white petrolatum, and zinc oxide), and sunscreen actives (such as aminobenzoic acid, avobenzone, cinoxate, dioxybenzone, homosalate, menthyl antranilate, octocrylene, octyl methoxycinnamate, octyl salicylate, oxybenzone, octyl dimethyl paraaminobenzoic acid, phenyl-benzimidazole sulfonic acid, sulisobenzene, titanium dioxide, trolamine salicylate, zinc oxide).

Natural fats, oils and waxes which are suitable for use as or as part of the topical applications in the present invention include, but are not limited to, avocado oil, apricot kernel oil, babassu oil, borage seed oil, camellia oil, canola oil, carrot oil, cashew oil, castor oil, cherry pit oil, chia oil, cod liver oil, coconut oil, corn oil, corn germ oil, cottonseed oil, evening primrose oil, glycosphingolipids, hazelnut oil, grape seed oil, hemp seed oil, human placenta lipids, jojoba oil, linseed oil, macadamia nut oil, meadowfoam seed oil, menhaden oil, mink oil, moringa oil, mortierella oil, neatsfoot oil, olive oil, ongokea oil, orange roughy oil, palm kernel oil, peanut oil, phospholipids, pistachio nut oil, poppy seed oil, rapeseed oil, rice bran oil, rose hip oil, safflower oil, hybrid safflower oil, sesame oil, shark liver oil, soybean oil, sunflower seed oil, hybrid sunflower seed oil, sweet almond oil, tall oil, triglycerides ($C_{12-18}$ acid triglycerides, caprylic/capric/lauric triglycerides, caprylic/capric/linoleic triglycerides, caprylic/capric/stearic triglycerides, lauric/palmitic/oleic triglycerides, oleic/linoleic triglycerides, tung oil, vegetable oil, veronia oil, walnut oil, wheat germ oil, cocoa butter, dairy butter, illipe butter, lanolin (wool fat), lanolin derivatives, lard, milk fat, shea butter, tallow, bayberry wax, beeswax, candelilla wax, carnuba wax, jojoba wax, japan wax, lanolin wax, mink wax, rice bran wax, shellac wax, spent grain wax, tribehenin, tricaprin, tricaprylin, triheptanoin, trihydroxymethoxystearin, trihydroxystearin, triisonananoin, triisostearin, trilaurin, trilinolein, trilinolein, trimyristryn, trioctanoin, triolein, trisebacin, tristearin, and triundecanoin.

Synthetic fats, oils and waxes which are suitable for use as or as part of the topical applications in the present invention include, but are not limited to, $C_{10-50}$ alkyl dimethicone waxes, ceresin wax, cetyl esters, epoxidized soybean oil, hydrogenated castor oil, hydrogenated castor oil laurate, hydrogenated coconut oil, hydrogenated cottonseed oil, hydrogenated $C_{12-18}$ triglycerides, hydrogenated fish oil, hydrogenated lard, hydrogenated menhanden oil, hydrogenated mink oil, hydrogenated orange roughy oil, hydrogenated palm kernel oil, hydrogenated palm oil, hydrogenated peanut oil, hydrogenated shark liver oil, hydrogenated soybean oil, hydrogenated tallow, hydrogenated vegetable oil, maleated soybean oil, microcrystalline waxes, mineral jelly, mineral oil, ozokerite wax, paraffin wax, PEG-6 beeswax, PEG-8 beeswax, petrolatum, PEG-5 castor oil, PEG-25 castor oil, PEG-40 castor oil, PEG-16 hydrogenated castor oil, PEG-40 hydrogenated castor oil, PPG-3 hydrogenated castor oil, synthetic beeswax, synthetic candelilla wax, synthetic carnuba wax, sythetic japan wax, synthetic jojoba wax, and synthetic wax.

Fatty acids which are suitable for use as part of the topical applications in the present invention include, but are not limited to, arachidic acid, arachidonic acid, behenic acid, behenoyl stearic acid, capric acid, caproic acid, caprylic acid, coconut acid, corn acid, cottonseed acid, hydrogenated coconut acid, hydrogenated menhaden acid, hydrogenated tallow acid, hydroxystearic acid, isostearic acid, lauric acid, linoleic acid, linseed acid, myristic acid, oleic acid, palmitic acid, palm kernel acid, perlargonic acid, ricinoleic acid, soy acid, stearic acid, tall oil acid, tallow acid, undecanoic acid, undecylenic acid, and wheat germ acid.

Fatty acid esters which are suitable for use as or as part of the topical applications in the present invention include, but are not limited to, $C_{12-15}$ alkyl benzoate, $C_{12-15}$ alkyl octanoate, behenyl behenate, behenyl benzoate, behenyl isostearate, capyrl isostearate, castor oil benzoate, cetyl acetate, cetyl lactate, cetyl octanoate, cetyl palmitate, cetyl ricinoleate, cetyl ricinoleate benzoate, decyl oleate, di-$C_{12-15}$ alkyl fumerate, dibehnyl fumerate, diethyl sebacate, diethylhexyl adipate, diethylhexyl maleate, diisocetyl adipate, dipropyl adipate, dipropylene glycol benzoate, diisostearyl maleate, diisopropyl adipate, diisopropyl dimer dilinoleate, diisopropyl sebacate, dimethyl lauramine isostearate, disostearyl maleate, dicapyrl maleate, dioctyl fumarate, ethylhexyl palmitate, ethylhexyl perlargonate, ethylhexyl stearate, isocetyl octanoate, isocetyl stearoyl stearate, isodecyl neopentanoate, isononyl isononoate, isostearyl neopentanoate, isostearyl benzoate, isostearyl stearoyl stearate, laureth-2 acetate, laureth-2 ethylhexanote, laureth-2 benzoate, lauryl behenate, lauryl lactate, methyl gluceth-20 benzoate, methyl acetyl ricinoleate, methyl palmitate, methyl stearate, myristyl lactate, myristyl myristate, myristyl stearate, neopentyl dicaprate, octyldodecyl myristate, neopentyl glycol dioctanoate/diisostearate, neopentyl glycol diisostearate/dioctanoate, octyidodecyl behenate, octyl benzoate, octyldodecyl benzoate, octyidodecyl erucate, octyidodecyl myristate, octyldodecyl neopentanoate, octyldodecyl ricinoleate, octyldodecyl stearoyl stearate, octyl hydroxystearate benzoate, octyl perlargonate, oleyl erucate, oleyl lactate, PPG-2 isoceteth-20 acetate, pentaerythirtyl ricinoleate, pentaerythirtyl tetraacetate, pentaerythirtyl tetraisostearate, pentaerythirtyl tetralaurate, pentaerythirtyl tetraethylhexanoate, pentaerythirtyl tetraperlargonate, pentaerythirtyl tetraisononanoate, poloxamer 105 benzoate, poloxamer 182, propylene glycol ceteth-3 acetate, propylene glycol isoceteth-3 acetate, propylene glycol myristyl ether acetate, propylene glycol dicaprylate/dicaprate, propylene glycol diperlargonate, stearyl benzoate, stearyl stearate, stearyl stearoyl stearate, tricapyrl citrate, tridecyl erucate, tridecyl trimellitate, triethylhexanoate, triethylhexyl trimellitate, triisocetyl citrate, trioctyldodecyl citrate, triisopropyl citrate, triisostearyl citrate, trimethylethane tribenzoate, trimethylolpropane, trioleyl citrate, isopropyl laurate, isopropyl myristate, isopropyl palmitate, and ethylhexy palmitate.

Polyhydroxy fatty acid esters which are suitable for use as or as part of the topical applications in the present invention include, but are not limited to, glyceryl behenate, glyceryl laurate, glyceryl monostearate, glyceryl monopalmitate, glyceryl monobehenate, glyceryl undecylenate, sucrose monostearate, sucrose distearate, sucrose monolaurate, sucrose dilaurate, sorbitan behenates, sorbitan palmitates, sorbitan stearates, and sorbitan tristearate.

Polyhydroxy fatty acid amides which are suitable for use as part of the topical applications in the present invention include, but are not limited to, lauryl methyl glucamide, lauryl methoxypropyl glucamide, cocoyl methyl glucamide, cocoyl methpxypropyl glucamide, palmityl methoxypropyl glucamide, tallowyl methoxypropyl glucamide, and tallowyl methyl glucamide.

Fatty alcohols which are suitable for use as part of the topical applications in the present invention include, but are not limited to, behenyl alcohol, cuts of alkyl alcohols (such as $C_{9-11}$ alcohols, $C_{12-13}$ alcohols, $C_{12-15}$ alcohols, $C_{12-16}$ alcohols, $C_{14-15}$ alcohols, and blends thereof), caprylic alcohol, cetearyl alcohol, cetyl alcohol, coconut alcohol, decyl alcohol, hydrogenated tallow alcohol, lauryl alcohol, myristyl alcohol, oleyl alcohol, palm alcohol, palm kernel alcohol, stearyl alcohol, tallow alcohol, and tridecyl alcohol.

Fatty alcohol ethoxylates which are suitable for use as part of the topical applications in the present invention include, but are not limited to, ceteth-10, cetearth-30, emulsifying wax NF, glycereth-7, glycereth-26, laureth-2, laureth-3, laureth-9, laureth-23, oleth-3, oleth-5, steareth-2, and steareth-10, steareth-20.

Essential oils which are suitable for use as or as part of the topical applications in the present invention include, but are not limited to, anise oil, balm mint oil, basil oil, bee balm oil, bergamot oil, birch oil, bitter almond oil, bitter orange oil, caledula oil, california nutmeg oil, caraway oil, cardamon oil, chamomile oil, cinnamon oil, clary oil, cloveleaf oil, clove oil, coriander oil, cypress oil, eucalyptus oil, fennel oil, gardenia oil, geranium oil, ginger oil, grapefruit oil, hops oil, hyptis oil, indigo bush oil, jasmine oil, juniper oil, kiwi oil, laurel oil, lavender oil, lemongrass oil, lemon oil, linden oil, lovage oil, mandarin orange oil, matricaria oil, musk rose oil, nutmeg oil, olibanum oil, orange flower oil, orange oil, patchouli oil, pennyroyal oil, peppermint oil, pine oil, pine tar oil, rose hips oil, rosemary oil, rose oil, rue oil, sage oil, sambucus oil, sandalwood oil, sassafras oil, silver fir oil, spearmint oil, sweet marjoram oil, sweet violet oil, tar oil, tea tree oil, thyme oil, wild mint oil, yarrow oil, and ylang ylang oil.

Polymers which are suitable for use as part of the topical applications in the present invention include, but are not limited to, acrylic acid copolymers, polyolefin resins, polyolefin polymers, ethylene/vinyl acetate copolymers, polyethylene, polydimethylsiloxanes (straight chain, branched chain, alky functionalized, amine functionalized, organo functionalized, phenyl functionalized, styryl functionalized), polydimethylsiloxane copolyols and polydimethylsiloxane copolyol esters (such as dimethicone copolyol phosphate).

Particulates which are suitable for use as or as part of the topical applications in the present invention include, but are not limited to, colloidal oatmeal, colloidal silica, corn starch, hectorite clays, kaolin, magnesium aluminum silicate, montmorillonite clays, titanium dioxide, titanium peroxide, talc, titanium salicylate, and zinc oxide.

Humectants which are suitable for use as part of the topical applications in the present invention include, but are not limited to, acetamide MEA, aloe vera gel, arginine PCA, chitosan PCA, copper PCA, corn glycerides, dimethyl imidazolidinone, erythrose, erythritol, fructose, glucamine, glucose, glucose glutamate, glucuronic acid, glutamic acid, glycereth-7, glycereth-12, glycereth-20, glycereth-26, glycerin, honey, hydrogenated honey, hydrogenated starch hydrolysate, hydrolyzed corn starch, galactose, lactamide MEA, lactic acid, lactose lysine, PCA, malitol, mannitol, maltodextrose, mannose, methyl gluceth-10, methyl glucet-20, PEG-2 lactamide, PEG-10 propylene glycol, polyamino sugar condensate, potassium PCA, propoxylated glycerin, propylene glycol, propylene glycol citrate, raftnose, realrose, saccharide hydrolysate, saccharide isomerate, sodium aspartate, sodium lactate, sodium PCA, sorbitan, sorbitol, sucrose, TEA-lactate, TEA-PCA, urea, xylose, and xylitol.

Sterols and sterol derivatives which are suitable for use as part of the topical applications in the present invention include, but are not limited to, beta sterols having a tail on the 17 position with no polar groups (including, but not limited to, cholesterol, sitosterol, stigmaserol, ergosterol) and sterols such as $C_{10-30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesterol octyldecanoate, dihydolanosterol, dihydrolanosteryl octyidecanoate, ergocalciferol, tall oil sterol, soy sterol acetate, lanasterol, soy sterol, avocado sterols, avocodin, and sterol esters.

The desired embodiments of the present invention will have topical applications which are petrolatum based. In one desired embodiment of the present invention the topical application may comprise a blend or combination of petrolatum, ozokerite wax, ethylene/vinyl acetate copolymer. In a second desired embodiment of the composite material, the topical application may be comprised of a blend or combination of petrolatum, ozokerite wax, sunflower seed oil, soy sterol, ethylene/vinyl acetate copolymer, dimethicone, and alkyl dimethicone wax. In yet another desired embodiment of the present invention, the topical application may comprise a blend or combination of petrolatum, ozokerite wax, sunflower seed oil, soy sterol, ethylene or vinyl acetate copolymer, dimethicone, alkyl dimethicone wax, colloidal silica, and montmorillonite clay.

In addition to the foregoing, it is desirable that the boundary layer 18 and the topical application 24 are compositions or composites which have a low affinity towards the other such that the transfer forces necessary to separate the topical application from the boundary layer are lower than the transfer forces necessary to separate the boundary substrate from the boundary layer. Low affinity between the boundary layer 18 and topical application 24 means that there are low cohesion forces acting between the boundary layer 18 and the topical application 24 which allow the topical application and boundary layer 24 to be separated with minimal force, such as that experienced during normal diaper or personal care absorbent product wear. While certain topical applications may be desirable for use in the composite material, a suitable boundary layer (i.e. having a low affinity to the topical application) must be available or an alternative topical application should be selected in order to achieve the desired results. In other words, in order to achieve the desired topical application transfer as well as the desired skin health or skin wellness benefits, the topical application selected for use in the invention should be selected for its skin health characteristics as well as its affinity to the compound or compounds which comprise the boundary layer.

Another desired embodiment of the present invention includes a boundary layer whose components begin to liquify or melt when exposed to a temperature of at least about 25° C. Although it is possible for the topical application 24 to be separated from all or part of the boundary layer 18 by transfer forces alone (i.e. without exposing the boundary layer to a certain range of temperatures), liquification of the boundary layer allows the topical application to be more readily transferred to the skin as the cohesive forces between the topical application and the boundary layer are weakened to a level which requires only minimal transfer forces to be exerted thereon to achieve separation of the application from the boundary layer. In other words, it is recognized that the use of a boundary layer whose compounds' affinity towards the topical application or another layer of the boundary layer is weakened when subjected to a certain temperature or range of temperatures can reduce the transfer forces necessary to achieve the desired separation as well as enable the use of compounds in the boundary layer and/or topical application which may not otherwise be desirable as a result of higher transfer forces (in an unheated state) necessary to cause separation. As above, it is desired that the boundary layer begin to melt or liquify at a temperature in the range of at least about 25° C. to about 45° C. It is more desirable that the boundary layer begin to melt or liquify at a temperature of about 25° C. to about 40° C., and is most desirable to begin to melt in the range of about 25° C. to about 37° C. The boundary layer need not melt or liquify completely. The boundary layer need only be liquified or melted to a point such that the transfer forces which are necessary to separate the topical application from the boundary layer have been reduced to a desired level. It is desired that the transfer forces which are necessary to separate the topical application from the boundary layer and/or substrate are generated or achieved during normal wear conditions, and more particularly during normal diaper wear conditions. While the primary emphasis of this description focuses on diapers, it is understood that the topical applications and boundary layers may be selected so that normal wear conditions of other personal care products are sufficient to promote transfer of the topical applications to the skin of a user.

Although references are made to the separation of the topical application from the boundary layer are made, it is noted that unless otherwise indicated, there need not be complete separation of the topical application from the boundary layer as the compounds of the boundary layer typically will not significantly impact the skin health or skin wellness characteristics or benefits of the topical application as it is transferred to the skin. Furthermore, reference to separation of the topical application from the substrate is not intended to suggest that the topical application is in direct contact with the substrate, but rather that the topical application has been separated from all or part of the boundary layer and hence from the substrate as well.

Furthermore, as suggested above and as shown in FIG. 6, in yet another embodiment designed to enhance transfer efficiency of the topical application, the boundary layer may include more than one layer of compounds having low affinity towards each other, thereby allowing the topical application and all or part of the second layer 68 of the boundary layer 18 to separate from the substrate and all or part of the first layer 66 of the boundary layer 18 rather than necessitating separation at the topical application/boundary layer interface 50. The ability to create boundary layer/boundary layer separation will allow the use of compounds in the boundary layer which, in light of the enhanced transfer efficiency goals of the invention, may otherwise be unsuitable for use (i.e. due to high affinity) with the topical application. That is, for example, the compounds of the first layer 66 of the boundary layer 18 may have a strong affinity towards the topical application 24, however, it may have a low or lower affinity to the second layer 68 of the boundary layer 18 which separates the first layer 66 of the boundary layer from the topical application 24, thereby reducing the transfer forces necessary to effectuate the separation and transfer of the topical application as well as allowing for the use of the compounds of the first layer 66 of the boundary layer where it might otherwise be undesirable to do so.

To further enhance transfer efficiency, the boundary layer 18 may be applied to the substrate and the topical application may be applied to the second layer 68 of the boundary layer 18 in a variety of patterns. To achieve maximum transfer efficiency it is not necessary for all of the first surface 14 of the substrate 12 to be covered by the boundary layer or all of the second surface 22 of the boundary layer 18 to be covered by the topical application. Although the figures illustrate the topical application as a continuous or substantially continuous application in the machine direction of the diaper, it is understood and contemplated that the topical application may be applied in any continuous or discontinuous pattern, including but not limited to, continuous or discontinuous lines in the machine direction, cross-direction, or diagonal orientations, sinusoidal waves or discrete dots, and the like, provided that the topical application is applied to a sufficient amount of boundary layer to facilitate the desired transfer.

The present invention also contemplates an embodiment of composite material of the present invention wherein the composite material comprises a substrate having a boundary layer applied thereto, and a topical application applied to the boundary layer wherein the topical application has a preferential affinity for a secondary surface, desirably the wearer's skin if the composite material is or is part of a personal care product. In this embodiment, the topical application separates from the substrate and/or boundary layer as a result of the topical application's preferential affinity for the secondary surface as opposed to exposure to heat or movement, as discussed above in connection with other embodiments of the present invention. The separation which occurs as a result of the preferential affinity of the topical application to the secondary surface is enabled or further enhanced by the inclusion of the boundary layer in the composite material, whereas the preferential affinity of the topical application may not have been sufficient to achieve the desired separation and transfer of topical application if the topical application had been applied directly to the substrate.

The invention is also directed to a method of forming a composite material adapted for uses such as transferring a topical application from a substrate to a surface. The method includes the provision of a substrate, the application of a boundary layer to the substrate, the application of a topical application to the boundary layer, and subjecting the boundary layer to at least one condition which facilitates separation of the topical application from the substrate and promotes transfer of the topical application to the surface. In one embodiment of the present invention, it is desired that the topical application compositions are transferable to the wearer's skin by normal contact, movement of the wearer, or the body heat of the wearer.

One embodiment of this method provides for the effective transfer of a topical application from a substrate to a user's skin, merely through the use of low transfer forces. This method includes providing a substrate, applying a boundary layer to the substrate, applying a topical application to the boundary layer, subjecting the boundary layer to transfer forces sufficient to allow the topical application to separate from the substrate or the boundary layer, and transferring the topical application to the skin which is adjacent to the topical application. Due to the composition of the boundary layer, the desired transfer forces which are sufficient to allow the desired transfer of the topical application are low and may be generated by the movements of a person wearing a product incorporating the composite material (i.e. a user's movement in a diaper).

The following examples are presented to provide a more detailed understanding of the invention. The specific materials and parameters are exemplary and are not intended to specifically limit the scope of the invention.

EXAMPLES

The Ink Rub Tester (Model #10-18-01, available from Testing Machines Inc. (TMI), having offices in Islandia, N.Y.) is an instrument used as a fast and reliable means of assessing the transfer amount of ointment from liner to baby's skin by gravimeteric means. Generally, the instrument functions by rubbing a block, covered with a receptor material, against a stable base covered in the treated liner material. The act of rubbing is intended to simulate the movement of the baby's skin against the inner diaper lining.

Figure 7:
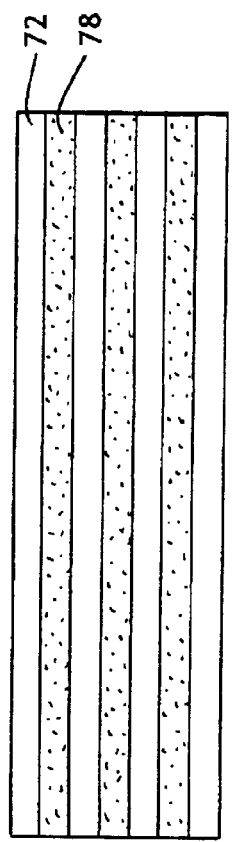
FIG. 7 illustrates the orientation of the slot-coated ointment lines as aligned lengthwise and centered as much as possible on the base material used in the examples.

In each of the Examples discussed below, the Ink Rub Tester (IRT) was used as prescribed in the instruction manual which accompanied the IRT from TMI, with the following exceptions: The receptor material 70 used was Typically Natural Silk Noil (Style #651) made by Testfabrics, Inc., and was cut to a sample size of 2"×6". The base material used in the Examples was a spunbond liner treated with 4 centered ointment stripes 72 (¼" wide and spaced by ¼"). The base material was dimensioned to approximately 3"×9", although the length of the base material was not critical so long as it covers the 2.5"×6" rubber pad. However, the slot-coated ointment lines were aligned lengthwise and centered as much as possible (see FIG. 7). Where a pre-treatment or boundary layer was added to the spunbond liner prior to the application of the ointment or transfer layer, the pre-treatment was generally applied in an amount equal to ⅒ the ointment add-on in stripes which have equal or slightly greater width than the stripes of ointment. The four pound weighted block of the IRT was selected for use during experimentation, as this was intended to more closely mimic the pressure that a baby will apply to a diaper while sitting or moving.

Prior to placing the receptor material 70 on the IRT, the receptor silk material 70 was weighed and its initial mass recorded. The material was folded in a tri-fold so as to ensure that all the material remained on top of the weighing plate. Care was also taken to ensure that no hanging threads existed, as those were likely to be torn off during operation of the instrument and influence later calculations. Additionally, examination gloves were worn at all times to prevent transfer of skin oils to the material, thereby avoiding the creation a faulty calculation of the change in mass.

Figure 8:
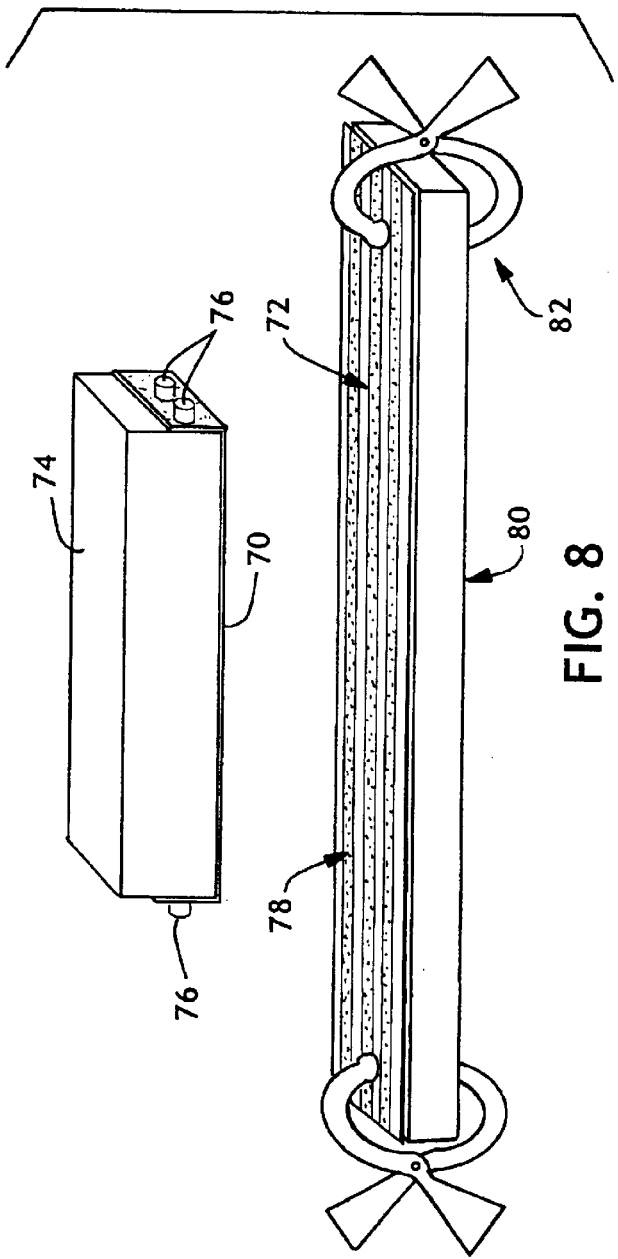
FIG. 8 is a schematic representation of the set-up for the Ink Rub Tester used in the examples.

Each material was then secured to the IRT. The receptor material 70 was spread out over the weighted block 74 and was held to the block by four magnets 76, with two magnets evenly spaced on either end of the block. Uniform tension throughout the receptor material 70 was sought, with the material being held tightly with no gaps between the block 74 and the fabric 70. However, extraordinary strain was not placed on the material. The base material 78, or liner, was centered upon the rubber pad 80. Attempts were made to remove all wrinkles in the liner 78, by spreading the fabric and attaching clips 82 at either end in order to prevent further movement of the fabric as seen in FIG. 8. The IRT was set to cycle 50 times at a rate of 100 cycles per minute. Once the prepared materials were secured to the IRT, the device was started and allowed to cycle. At the completion of the selected number of cycles, the liner was removed and thrown away, while the receptor material 70 was removed and was again tri-folded and its weight recorded. The change in weight is defined as the difference between the initial and final weight of the receptor material 70, and is representative of the amount of material transferred. Generally, the procedure was repeated 10 times to obtain a statistically significant average amount of material transferred, however, in some of the examples the procedure was repeated only 6 times.

Example 1

In Example 1, the procedure described above was used, with the exception that neither a boundary layer or transfer layer was applied to the base material (liner). Example 1 was intended to function as a control, i.e. untreated nonwoven liner. The results of this example are found in Table 1 and illustrate that the rubbing results in the loss of receptor material. These results would suggest that in those instances that a diaper does not contain an ointment, lotion or like applied to the surface of the diaper liner that the rubbing which a baby's skin experiences during diaper wear will result in the abrasion of the baby's skin or loss of mass.

TABLE 1

| Rep. no | $W_o$ (g) | $W_f$ (g) | $\Delta W$ (g) |
| --- | --- | --- | --- |
| 1 | 2.0896 | 2.089 | −0.0006 |
| 2 | 1.9714 | 1.9706 | −0.0008 |
| 3 | 1.9775 | 1.9765 | −0.001 |
| 4 | 1.9544 | 1.9535 | −0.0009 |
| 5 | 2.0984 | 2.0974 | −0.001 |
| 6 | 1.956 | 1.9553 | −0.0007 |
| 7 | 1.9993 | 1.9973 | −0.002 |
| 8 | 1.9617 | 1.961 | −0.0007 |
| 9 | 2.0616 | 2.0584 | −0.0032 |
| 10 | 2.0095 | 2.0082 | −0.0013 |
| | | Average | −0.00122 |
| | | Standard Deviation | 0.0008053 |

Example 2

Receptor material and base material having the same general characteristics as the materials described in Example 1 were tested. The materials were substantially the same as in Example 1, except that a transfer layer in the form of an ointment was applied to the base material in the manner indicated above. In this example, the ointment used generally included petrolatum, an emollient, a wax, an oil, a commercial lipid mix and optionally a vicosity enhancer and no boundary layer was added to the liner. The ointment applied to the base material in an amount of about 3.67 milligrams (mg) per square inch or about 0.25 grams of lotion per 68 square inches of liner material (or 4"×17"). The results are set forth in Table 2 below.

TABLE 2

| Rep. No | $W_o$ (g) | $W_f$ (g) | $\Delta W$ (g) |
|---|---|---|---|
| 1 | 1.9280 | 1.9467 | 0.0187 |
| 2 | 2.0595 | 2.0741 | 0.0146 |
| 3 | 2.0600 | 2.0768 | 0.0168 |
| 4 | 2.0763 | 2.0928 | 0.0165 |
| 5 | 2.0589 | 2.0745 | 0.0156 |
| 6 | 1.9967 | 2.0141 | 0.0174 |
| 7 | 1.8920 | 1.9082 | 0.0162 |
| 8 | 1.9515 | 1.9680 | 0.0165 |
| 9 | 2.1100 | 2.1258 | 0.0158 |
| 10 | 2.0770 | 2.0894 | 0.0124 |
| | | Average | 0.01605 |
| | | Standard Deviation | 0.0016841 |

Example 3

Receptor material and base material having the same general characteristics as the materials described in Example 1 were tested. The materials were substantially the same as in Example 1, except that a transfer layer in the form of an ointment was applied to the base material in the manner indicated above. In this example, the same ointment as that used in Example 2, and the spunbond liner material (base material) was pre-treated with a blend of Ahcovel and Glucopon in an amount of about 0.35% by weight with respect to the weight of the liner material (or 0.0076 mg per square inch of liner material) with the pre-treatment consisting of 3 parts Ahcovel and 1 part Glucopon. The ointment applied to the base material in an amount of about 3.67 milligrams per square inch of liner material or about 0.25 grams of lotion per 68 square inches of liner material. The results are set forth in Table 3 below.

TABLE 3

| Rep. No | $W_o$ (g) | $W_f$ (g) | $\Delta W$ (g) |
|---|---|---|---|
| 1 | 1.2526 | 1.2683 | 0.0157 |
| 2 | 1.2525 | 1.2667 | 0.0142 |
| 3 | 1.1951 | 1.2113 | 0.0162 |
| 4 | 1.2727 | 1.2896 | 0.0169 |
| 5 | 1.2617 | 1.2764 | 0.0147 |
| 6 | 1.2588 | 1.2761 | 0.0173 |
| 7 | 1.2574 | 1.273 | 0.0156 |
| 8 | 1.270 | 1.2841 | 0.0141 |
| 9 | 1.3143 | 1.3307 | 0.0164 |
| 10 | 1.2117 | 1.226 | 0.0143 |
| | | Average | 0.01554 |
| | | Standard Deviation | 0.00117 |

Example 4

Receptor material and base material having the same general characteristics as the materials described in Example 1 were tested. The materials were substantially the same as in Example 1, except that a transfer layer in the form of an ointment was applied to a boundary layer which was applied to the base material in the manner indicated above. In this example, the ointment used was as that used in Examples 2 and 3, and was slot-coated onto a boundary layer of Cetiol 1414E. The Cetiol was applied to the base material in an amount of about 0.36 milligrams per square inch or about 0.025 grams of Cetiol 1414E per 68 square inches of liner material. The layer of ointment was applied to the layer of Cetiol in an amount of about 3.67 milligrams per square inch or about 0.25 grams square inches of liner material. The results are set forth in Table 4 below.

TABLE 4

| Rep. No | $W_o$ (g) | $W_f$ (g) | $\Delta W$ (g) |
|---|---|---|---|
| 1 | 2.0875 | 2.1165 | 0.0290 |
| 2 | 1.9977 | 2.0288 | 0.0311 |
| 3 | 1.9910 | 2.0183 | 0.0273 |
| 4 | 1.9212 | 1.9523 | 0.0311 |
| 5 | 2.0445 | 2.0745 | 0.0300 |
| 6 | 2.0036 | 2.0304 | 0.0268 |
| 7 | 2.1446 | 2.1755 | 0.0309 |
| 8 | 2.1556 | 2.1865 | 0.0309 |
| 9 | 2.1200 | 2.1522 | 0.0322 |
| 10 | 2.1409 | 2.1713 | 0.0304 |
| | | Average | 0.02997 |
| | | Standard Deviation | 0.00175 |

Example 5

Receptor material and base material having the same general characteristics as the materials described in Example 1 were tested. The materials were substantially the same as in Example 1, except that a transfer layer in the form of an ointment was applied to a boundary layer which was applied to the base material in the manner indicated above. In this example, the ointment used comprised a mixture of Tween 20 (available from Uniqema, having offices in New Castle Del.) and Tween 40 (available from Uniqema), in a 1:1 ratio. The layer of Tween 20 and Tween 40 are applied on top of the liner material, which acts as a boundary layer, in an amount of about 0.36 milligrams per square inch or about 0.025 grams per 68 square inches of liner material. The layer of ointment was applied to the layer of Tween 20/Tween 40 in an amount of about 3.67 milligrams per square inch or about 0.25 grams of lotion per 68 square inches of liner material The results are set forth in Table 5 below.

TABLE 5

| Rep. No | $W_o$ (g) | $W_f$ (g) | $\Delta W$ (g) |
|---|---|---|---|
| 1 | 2.1351 | 2.1573 | 0.0222 |
| 2 | 2.0237 | 2.0471 | 0.0234 |
| 3 | 2.0373 | 2.0632 | 0.0259 |
| 4 | 2.1978 | 2.2228 | 0.025 |
| 5 | 1.9972 | 2.0202 | 0.023 |
| 6 | 2.0056 | 2.0281 | 0.0225 |
| 7 | 2.0409 | 2.0631 | 0.0222 |
| 8 | 1.9649 | 1.9878 | 0.0229 |
| 9 | 1.983 | 2.0044 | 0.0214 |
| 10 | 2.0837 | 2.106 | 0.0223 |
| | | Average | 0.02308 |
| | | Standard Deviation | 0.0013782 |

Example 6

Receptor material and base material having the same general characteristics as the materials described in Example 1 were tested. In this example, the boundary layer used was the same as that used in Example 5 (comprising a mixture of Tween 20 and Tween 40), however, unlike Example 5, no ointment was applied to the boundary layer. The layer of Tween 20 and Tween 40 was applied to the base material in an amount of about 0.36 milligrams per square inch or about 0.025 grams of Tween20/Tween 40 per 68 square inches of base liner material. The results are set forth in Table 6 below.

TABLE 6

| Rep. No | $W_o$ (g) | $W_f$ (g) | $\Delta W$ (g) |
|---|---|---|---|
| 1 | 1.4687 | 1.4708 | 0.0021 |
| 2 | 1.5124 | 1.5137 | 0.0013 |
| 3 | 1.4922 | 1.4939 | 0.0017 |
| 4 | 1.5052 | 1.5052 | 0 |
| 5 | 1.4979 | 1.4985 | 0.0006 |
| 6 | 1.4655 | 1.4658 | 0.0003 |
| 7 | 1.5656 | 1.5673 | 0.0017 |
| 8 | 1.5066 | 1.5073 | 0.0007 |
| 9 | 1.5221 | 1.5229 | 0.0008 |
| 10 | 1.5671 | 1.5681 | 0.001 |
| | | Average | 0.00102 |
| | | Standard Deviation | 0.0006713 |

Example 7

Receptor material and base material having the same general characteristics as the materials described in Example 1 were tested. The materials were substantially the same as in Example 1, except that Cetiol was applied to the base material in the manner indicated above. The layer of Cetiol 1414E was applied to the base material in an amount of about 0.36 milligrams per square inch or about 0.025 grams of Cetiol per 68 square inches of base liner material. The results are set forth in Table 7 below.

TABLE 7

| Rep. No | $W_o$ (g) | $W_f$ (g) | $\Delta W$ (g) |
|---|---|---|---|
| 1 | 1.5645 | 1.5671 | 0.0026 |
| 2 | 1.5109 | 1.5141 | 0.0032 |
| 3 | 1.5390 | 1.5415 | 0.0025 |
| 4 | 1.5443 | 1.5461 | 0.0018 |
| 5 | 1.5439 | 1.5458 | 0.0019 |
| 6 | 1.4525 | 1.4548 | 0.0023 |
| 7 | 1.4852 | 1.4876 | 0.0024 |
| 8 | 1.4148 | 1.4167 | 0.0019 |
| 9 | 1.5571 | 1.5593 | 0.0022 |
| 10 | 1.4940 | 1.4960 | 0.0020 |
| | | Average | 0.00228 |
| | | Standard Deviation | 0.0004237 |

Example 8

Receptor material and base material having the same general characteristics as the materials described in Example 1 were tested. The materials were substantially the same as in Example 1, except that a transfer layer in the form an ointment was applied to a Cetiol 1414E boundary layer which was pre-applied to the base material. In this example, the ointment comprised petrolatum. The petrolatum was applied to a cetiol-pretreated spunbond liner, similar to that of Example 6. In each instance of this example the petolatum was applied to the liner by way of ink-jet printing. This example was repeated with four times with increasing amounts of Cetiol add-on level. The first run included a spunbond liner with 0 wt % Cetiol add-on, the second run 1 wt % Cetiol with respect to the weight of the base liner material (or 0.22 mg per square inch of base liner material), the third run 2% Cetiol add-on (or 0.44 mg per square inch of base liner material) and the fourth run 3% Cetiol add-on (or 0.65 mg per square inch of base liner material). The layer of petrolatum was applied to the base material in an amount of about 3.67 milligrams per square inch or about 0.25 grams of petrolatum per 68 square inches of base liner material. The results are set forth in Table 8 below.

TABLE 8

| | Cetiol (0%) | Cetiol (1%) | Cetiol (2%) | Cetiol (3%) |
|---|---|---|---|---|
| 1 | 0.0141 | 0.0154 | 0.0186 | 0.0195 |
| 2 | 0.0141 | 0.0161 | 0.0193 | 0.0353 |
| 3 | 0.0143 | 0.0144 | 0.0156 | 0.0247 |
| 4 | 0.0129 | 0.0149 | 0.0182 | 0.022 |
| 5 | 0.0162 | 0.0145 | 0.0213 | 0.0319 |
| 6 | 0.0162 | 0.0178 | 0.0168 | 0.0232 |
| 7 | 0.0136 | | | |
| 8 | 0.0146 | | | |
| 9 | 0.0144 | | | |
| 10 | 0.0154 | | | |
| Average | 0.01458 | 0.01551667 | 0.0183 | 0.0261 |
| Standard Deviation | 0.00106854 | 0.00128284 | 0.001982 | 0.006148 |

The results of Example 8 are further illustrated in Table 9.

TABLE 9

Petrolatum Transfer Efficiency As a Function of Cetiol Add-On

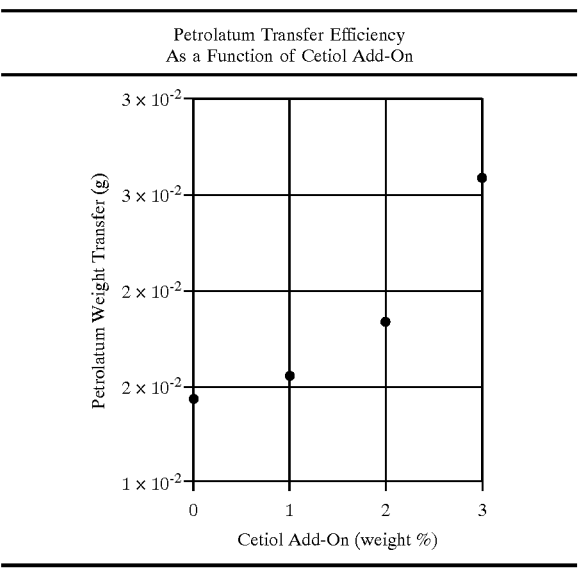

While the present invention has been described in connection with certain desired embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A composite material comprising:

a substrate having a first and a second surface;

a boundary layer comprising a hydrocarbon emollient on the first surface at the substrate; and an overlayer comprising a topical application on the surface of the boundary layer opposite of the substrate;

wherein the transfer forces necessary to separate the topical application from the boundary layer are lower than the transfer forces necessary to separate the substrate from the boundary layer, whereby transfer efficiency of the topical application is enhanced wherein the substrate is a top sheet.

2. The composite material of claim 1 wherein the boundary layer and the topical application have a low affinity towards the other.

3. The composite material of claim 1 for application to skin wherein the boundary layer has a lower melt temperature than the substrate, whereby the boundary layer liquifies when exposed to a temperature of at least about 25° C., thereby reducing the transfer forces necessary to transfer the topical application to the skin.

4. The composite material of claim 1 wherein the boundary layer is applied to the substrate during melt processing of the substrate or is applied topically after melt processing.

5. The composite material of claim 1 wherein the boundary layer is comprised of one or more compositions.

6. The composite material of claim 5 wherein the boundary layer is further comprised of multiple layers of one or more compositions.

7. The composite material of claim 6 wherein the compositions comprising the boundary layer have low affinity to each other and may be separated from each other with low transfer forces.

8. The composite material of claim 1 for application to skin wherein the topical application comprises a lotion, an ointment, a particulate, or a combination thereof.

9. The composite material of claim 8 wherein the lotion or ointment is selected from a group consisting of natural fats and oils and waxes, synthetic fats and oils and waxes, fatty acids, fatty acid esters, polyhydroxy fatty acid esters, polyhydroxy fatty acid amides, fatty alcohols, fatty alcohol ethoxytates, essential oil, polymers, sterols and sterol derivatives, humectants, and combinations thereof.

10. The composite material of claim 8 wherein the lotion or ointment is petrolatum based.

11. The composite material of claim 8 wherein the lotion or ointment is comprised a blend or combination of petrolatum, ozokerite wax and ethylene/vinyl acetate copolymer.

12. The composite material of claim 8 wherein the lotion or ointment is comprised a blend or combination of petrolatum, ozokerite wax, sunflower seed oil, soy sterol, ethylene/vinyl acetate copolymer, dimethicone, and alkyl dimethicone wax.

13. The composite material of claim 8 wherein the lotion or ointment is comprised a blend or combination of petrolatum, ozokerite wax, sunflower seed oil, soy sterol, ethylene/vinyl acetate copolymer, dimethicone, alkyl dimethicone wax, colloidal silica, and montmorillonite clay.

14. The composite material of claim 1 wherein the substrate is selected from woven fabrics, knit fabrics, nonwoven fabrics, foams, films and paper materials.

15. The composite material of claim 1 wherein the substrate comprises a nonwoven web.

16. The composite material of claim 15, wherein the nonwoven web comprises a spunbond web, a meltblown web, a coformed web or a bonded carded web.

17. The composite material of claim 15 wherein said substrate comprises a multi-layer laminate.

18. The composite material of claim 1 wherein the boundary layer is applied only to a portion of the substrate.

19. The composite material of claim 1 wherein the topical application is applied only to a portion of the exposed boundary layer.

20. The composite material of claim 19 wherein the topical application is applied to the boundary layer in strips.

21. A personal care product comprising the composite material of claim 1.

22. The personal care product of claim 21, wherein the personal care product is selected from a diaper, training pant, absorbent underpant, adult incontinence product, sanitary wipe, wet wipes, feminine hygiene product, wound dressing and bandage.

23. A method of forming a composite material adapted for transferring a topical application from a substrate to a surface, said method comprising:
    a substrate having a first and a second surface;
    a boundary layer comprising a hydrocarbon emollient on the first surface of the substrate; and
    an overlayer comprising a topical application on the surface of the boundary layer opposite of the substrate;
    wherein the transfer forces necessary to separate the topical application from the boundary layer are lower than the transfer forces necessary to separate the substrate from the boundary layer, whereby transfer efficiency of the topical application is enhanced, wherein the substrate is a top sheet.

24. The method of claim 23, wherein the method further comprises subjecting the boundary layer to at least one condition which facilitates separation of the topical application from the substrate and promotes transfer of the topical application to the surface.

25. The method of claim 24 wherein the step of subjecting the boundary layer to at least one condition which facilitates separation of the topical application from the substrate and promotes transfer of the topical application to the surface comprises:
    subjecting the boundary layer to transfer forces sufficient to separate the topical application from all or part of the boundary layer.

26. The method of claim 24 wherein the step of subjecting the boundary layer to at least one condition which facilitates separation of the topical application from the substrate and promotes transfer of the topical application to the surface may further comprise:
    exposing the boundary layer to a temperature sufficient to permit the boundary layer to liquify, whereby the boundary layer liquifies thereby allowing the topical application to be transferred to the surface.

27. The composite material of claim 23 wherein the boundary layer is applied to the substrate during melt precessing of the substrate or is applied topically after melt processing.

28. The method of claim 26 for application to skin wherein the temperature sufficient to permit the boundary layer to liquify is at least about 25° C.

29. The method of claim 25 wherein the transfer forces sufficient to allow the topical application to separate from all or part of the boundary layer is provided by the movement of a person using the substrate.

30. The method of claim 23 wherein the boundary layer is applied to the substrate in a variety of patterns.

31. The method of claim 23 wherein the topical application is applied to the boundary layer in a variety of patterns.

32. The method of claim 23 wherein the surface is the outermost exposed layer of dermis or epidermis.

33. The method of claim 23 wherein the substrate is a nonwoven web.

34. The method of claim 23 wherein the boundary layer consists essentially of a hydrocarbon emollient.

35. The method of claim 23 wherein the boundary layer comprises myristyl myristate.

36. The method of claim 23 wherein the boundary layer consists essentially of myristyl myristate.

37. The composite material of claim 1 wherein the boundary layer consists essentially of a hydrocarbon emollient.

38. The composite material of claim 1 wherein the boundary layer comprises myristyl myristate.

39. The composite material of claim 1 wherein the boundary layer consists essentially of myristyl myristate.

\* \* \* \* \*